(12) United States Patent
Sia et al.

(10) Patent No.: US 9,268,911 B2
(45) Date of Patent: Feb. 23, 2016

(54) FIELD OPTIMIZED ASSAY DEVICES, METHODS, AND SYSTEMS

(71) Applicant: The Trustees of Columbia University in the City of New York, New York, NY (US)

(72) Inventors: Samuel K. Sia, New York, NY (US); Mario Matteo Modena, Cirie (IT); Paolo Cadinu, Nuoro (IT); Keith Yeager, Jersey City, NJ (US); Yuk Kee Cheung Poh, Cambridge, MA (US); Robert Houghtaling, Kennett Square, PA (US); Tassaneewan Laksanasopin, New York, NY (US); Curtis D. Chin, San Diego, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/339,069

(22) Filed: Jul. 23, 2014

(65) Prior Publication Data
US 2014/0333453 A1 Nov. 13, 2014

Related U.S. Application Data

(63) Continuation of application No. PCT/US2013/023015, filed on Jan. 24, 2013.

(60) Provisional application No. 61/590,326, filed on Jan. 27, 2012, provisional application No. 61/591,319, filed on Jan. 27, 2012, provisional application No. 61/591,475, filed on Jan. 27, 2012.

(51) Int. Cl.
*G06F 19/00* (2011.01)
*G06F 21/60* (2013.01)
*H04L 9/14* (2006.01)

(52) U.S. Cl.
CPC .......... *G06F 19/3418* (2013.01); *G06F 19/322* (2013.01); *G06F 21/602* (2013.01); *H04L 9/14* (2013.01)

(58) Field of Classification Search
CPC . G06F 19/3418; G06F 19/322; G06F 21/602; H04L 9/14; B01L 3/50273
USPC ................ 340/870.01–870.44; 506/9; 705/51
See application file for complete search history.

(56) References Cited

U.S. PATENT DOCUMENTS 6,137,527 A 10/2000 Abdel-Malek et al.
6,716,002 B2 4/2004 Higashino
(Continued)

OTHER PUBLICATIONS http://www.globalsecurity.org/space/systems/iridium.htm, Enhanced Mobile Satellite Services (EMSS) Iridium, page last modified on Jul. 21, 2011.*
(Continued)

*Primary Examiner* — Jennifer Mehmood
*Assistant Examiner* — Omar Casillashernandez
(74) *Attorney, Agent, or Firm* — Miles & Stockbridge, PC; Mark A. Catan

(57) ABSTRACT

A portable unitary device handheld diagnostic device can be operated with minimal power requirement and provides ease of operation as well as low cost communication of diagnostic data from remote locations. The device can provide nucleic-acid based diagnostics with minimal training, little to no sample preparation, and generates diagnostic data in about 45 minutes. A system can enable point of care transmission from any location globally using a low cost satellite-based data link technique, for example, Short Burst Data (SBD), combined with data encoding.

19 Claims, 8 Drawing Sheets

(56) References Cited

U.S. PATENT DOCUMENTS

| | | | |
|---|---|---|---|
| 6,743,399 | B1 | 6/2004 | Weigl et al. |
| 6,767,194 | B2 | 7/2004 | Jeon et al. |
| 7,284,966 | B2 | 10/2007 | Xu et al. |
| 7,420,659 | B1* | 9/2008 | Cabuz et al. ............ 356/39 |
| 7,526,741 | B2 | 4/2009 | Lee et al. |
| 7,942,160 | B2 | 5/2011 | Jeon et al. |
| 8,260,551 | B2* | 9/2012 | Janky et al. ............. 701/469 |
| 8,652,852 | B2 | 2/2014 | Beebe et al. |
| 2004/0183724 | A1 | 9/2004 | Sheynblat |
| 2005/0250995 | A1* | 11/2005 | Quy ....................... 600/300 |
| 2006/0092029 | A1* | 5/2006 | Browne et al. ............. 340/573.1 |
| 2006/0252069 | A1 | 11/2006 | Zhang et al. |
| 2007/0082340 | A1 | 4/2007 | Huletsky et al. |
| 2007/0184463 | A1 | 8/2007 | Molho et al. |
| 2008/0023388 | A1 | 1/2008 | Cho et al. |
| 2009/0197275 | A1 | 8/2009 | Schoenbrunner et al. |
| 2009/0220387 | A1 | 9/2009 | Guu et al. |
| 2009/0221431 | A1* | 9/2009 | Yoo ....................... 506/9 |
| 2010/0022186 | A1* | 1/2010 | Walley ..................... 455/12.1 |
| 2010/0074253 | A1* | 3/2010 | Cheriyath et al. ............ 370/389 |
| 2010/0152432 | A1 | 6/2010 | Wu |
| 2010/0234237 | A1* | 9/2010 | Yoo ....................... 506/9 |
| 2011/0021374 | A1* | 1/2011 | Lee ....................... 506/9 |
| 2011/0144451 | A1* | 6/2011 | Robertson ................. 600/300 |
| 2011/0207619 | A1* | 8/2011 | Ehben et al. ............ 506/9 |
| 2011/0251960 | A1* | 10/2011 | Holla et al. ............ 705/51 |
| 2011/0269138 | A1 | 11/2011 | Wiezer |

OTHER PUBLICATIONS

Abate et al., "Syringe-Vacuum Microfluidics: A Portable Technique to Create Monodispers Emulsions," *Biomicrofluidics*, Mar. 2011, 5(014107): pp. 1-8.

Iwai et al., "Finger-Powered MicroDroplet Generator," *The 16th International Solid-State Sensors, Actuators, and Microsystems Conference (Transducers 2011)*, Jun. 2011, pp. 230-233.

Zahn et al., "Continuous On-Chip MicroPumping Through a MicroNeedle," *The 14th International Conference on MicroElectroMechanical Systems (MEMS)*, Jan. 2001, pp. 503-506.

Ferguson et al., "Genetic Analysis of H1N1 Influenza Virus from Throat Swab Samples in a Microfluidic System for Point-of-Care Diagnostics," *Journal of the American Chemical Society*, May 2011, 133: pp. 9129-9135.

GlobalSecurity.org, "Enhanced Mobile Satellite Services (EMSS) Iridium," Jul. 21, 2011 [online], [retrieved on May 15, 2013]. Retrieved from the Internet: <URL: http://ww.globalsecurity.org/space/systems/iridium.htm>.

International Search Report and Written Opinion for International Application No. PCT/US13/23015, mailed May 31, 2013.

\* cited by examiner

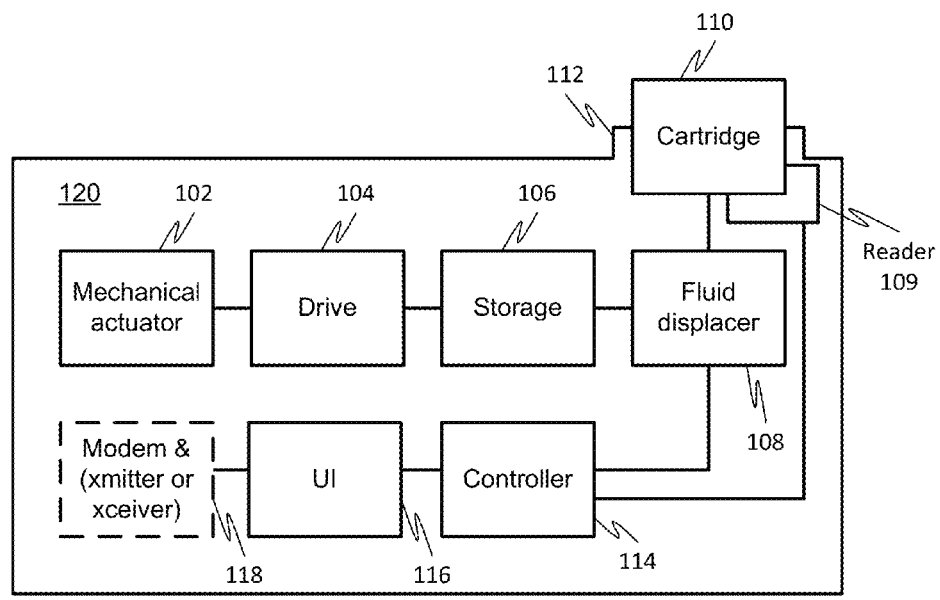
Fig. 1A
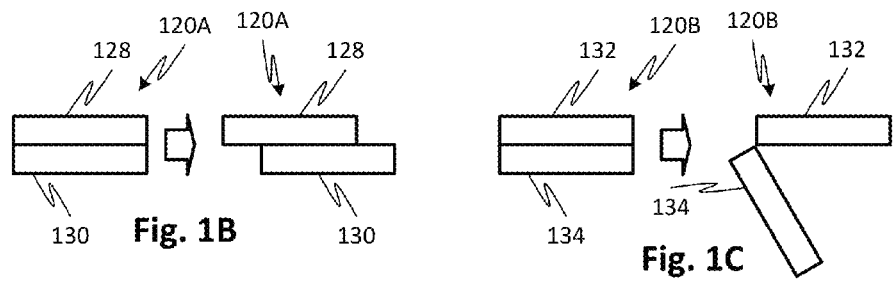
Fig. 1B          Fig. 1C
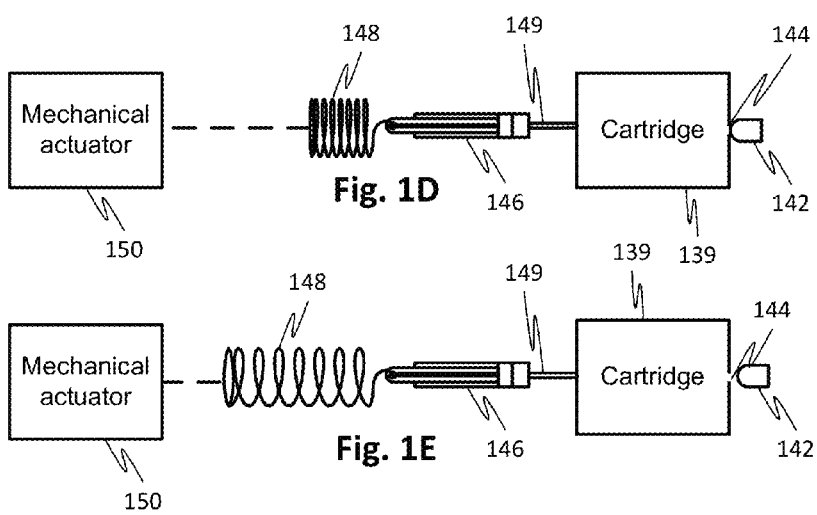
Fig. 1D
Fig. 1E

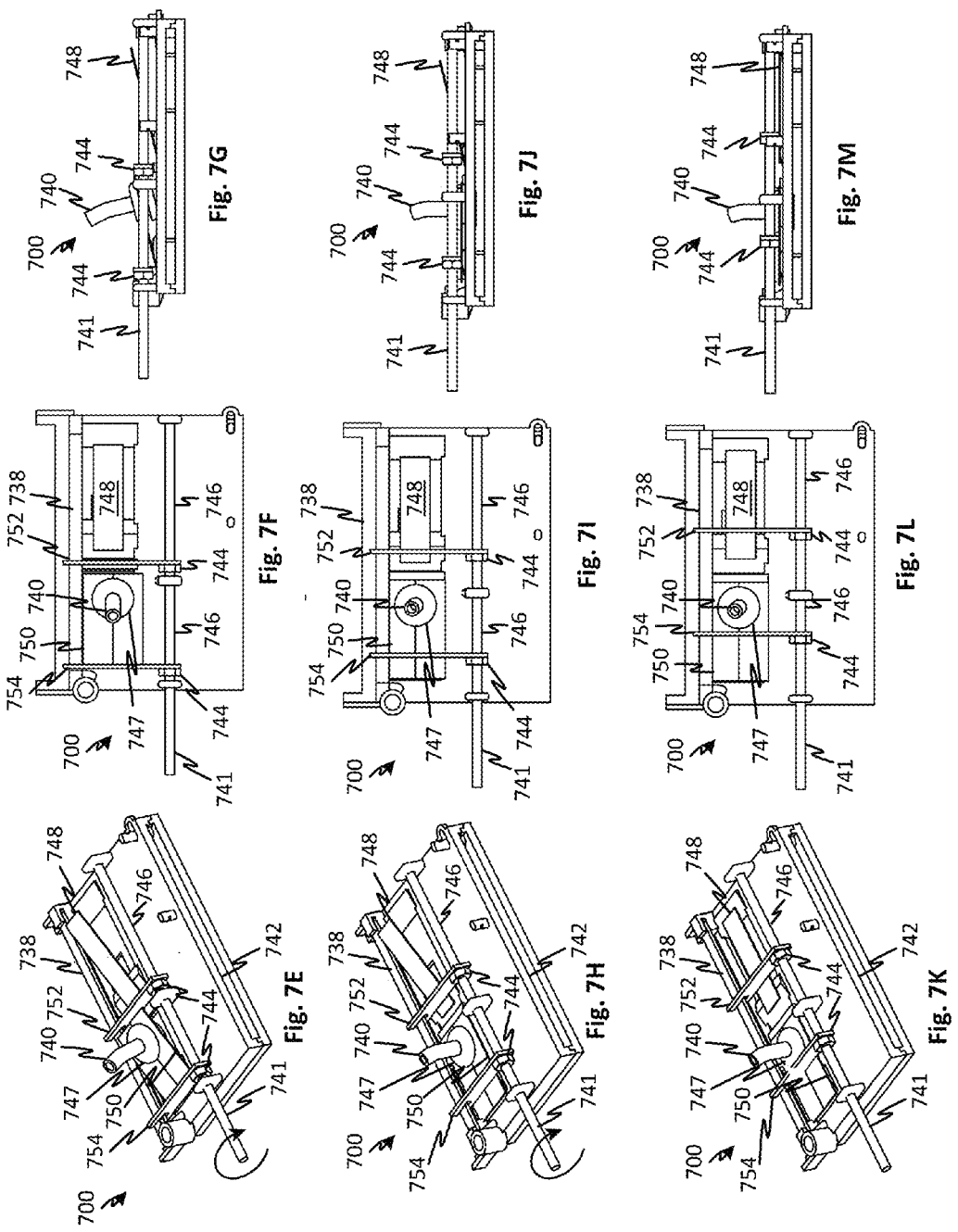

FIELD OPTIMIZED ASSAY DEVICES, METHODS, AND SYSTEMS

CROSS-REFERENCE TO RELATED APPLICATIONS

The present application is a continuation of International Application No. PCT/US13/23015, filed Jan. 24, 2013, which claims the benefit of U.S. Provisional Application No. 61/591,475, filed Jan. 27, 2012, U.S. Provisional Application No. 61/591,319, filed Jan. 27, 2012, and U.S. Provisional Application No. 61/590,326, filed Jan. 24, 2012, all of which are hereby incorporated by reference herein in their entireties.

STATEMENT REGARDING FEDERALLY SPONSORED RESEARCH

This invention was made with government support under 5R41NR10753 awarded by the National Institutes of Health (NIH). The government has certain rights in the invention.

BACKGROUND

Current handheld diagnostic systems require a significant power supply to move fluids around the chip. Microfluidic assay systems are frequently, at least partly, pneumatically-driven. A pump is connected to a microfluidic circuit and energized to move fluid through a microfluidic circuit. Valves may be provided externally to control the flow. Micropumps of suitable design for assay devices are relatively large and use a power source.

Microfluidic assay systems have employed magnetic beads with surfaces with probes to combine with target biomolecules or cells are trapped in a flow passage by a magnet. The beads are combined with a solution containing the target biomolecules or cells and the combination flowed through the chamber such that the magnetic beads remain in the chamber.

SUMMARY

A portable unitary device handheld diagnostic device can be operated with minimal power requirement and provides ease of operation as well as low cost communication of diagnostic data from remote locations. In an embodiment, the device provides nucleic-acid based diagnostics with minimal training, little to no sample preparation, and generates diagnostic data in about 45 minutes. In embodiments, a system enables point of care transmission from any location globally using a low cost satellite-based data link technique, for example, Short Burst Data (SBD), combined with data encoding.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 1A shows a general embodiment of a diagnostic system according to embodiments of the disclosed subject matter.

FIGS. 1B and 1C show kinematic mechanical input features for a diagnostic system according to further embodiments of the disclosed subject matter.

FIGS. 1D and 1E show a mechanical system which may be provided in embodiments of diagnostic system, according to further embodiments of the disclosed subject matter.

FIGS. 7E through 7M illustrate engagement system features of some embodiments of diagnostic systems elsewhere disclosed herein.

DETAILED DESCRIPTION

Figure 2A:
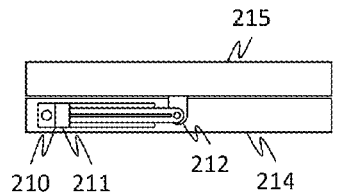
FIGS. 2A through 2E show further mechanical system features which may be provided in embodiments of diagnostic system, according to further embodiments of the disclosed subject matter.

Methods, devices, systems and kits for performing biological particle assays are suitable for use in low resource remote environments. The described technology provides zero power fluid transport system for driving a microfluidic circuit, a magnetic particle system for target biological particle capture, and a low cost system for communicating diagnostic data. The system may be applied in a handheld, nucleic-acid based diagnostic device for rapid diagnosis of MRSA in point of care settings, for example. The embodiments may be operable with minimal training, require no sample preparation, and deliver results quickly (e.g., in less than an hour).

The system provides for and controls fluid handling in microfluidic cassettes with zero-power consumption required for driving the fluid circuit. The zero power fluid transport is enabled by the use of a system that stores mechanical energy input manually by the user and tapping into that energy to transport the fluid through the circuit. In embodiments, the manual input stores a vacuum in a reservoir which is selectively connected to a microfluidic cassette to run an assay process. Control may be provided by an electrical subsystem which is very low power because there is no need for a fluid pump.

The disclosed embodiments are suitable for handheld battery powered devices. The disclosed system embodiments may include components that can work together in combination to form a unitary device, or function independently. For example, the system for communicating diagnostic data may be implemented with a separate modem attached to a portable computer or as an embedded system as part of a handheld diagnostic device. The fluid transport, magnetic bead capture, and data transmission subsystems will next be described in turn.

The fluid transport pump does not require any voltage supply and thus achieves zero electrical power consumption. Known pumps used for microfluidic diagnostic systems require a voltage supply. Since battery life is a key parameter for any portable device, the consumption related to an electric pump represents a very strong limiting factor for the battery life of the entire device itself. In principle, a manually driven pump has the potential to provide adequate power without undue energy demand on the user. The control and interface are addressed in the following description along with ergonomic factors.

According to embodiments, the fluid transport device includes a pump that is capable of achieving a positive or negative pressure range of −10 kPa to +10 kPa. Preferably, as mentioned, this is provided with zero power consumption. In addition, the fluid transport device may be configured so that it does not introduce vibration or pulsatile variation in flow during the driving of fluid through the microfluidic circuit. The fluid transport device may also beneficially avoid the generation of electrical interference. The fluid transport may be low cost, lightweight, and essentially no-maintenance; for example, it may require no lubrication. The fluid transport device may also be non-metallic and operable in any orientation. The general configuration may permit customization to any desired range of pressure or displacement up to the constraints of usability based on manual power input.

In an embodiment, the zero power fluid transport device is based on a vacuum pump and vacuum storage embodied by one or more syringe-type pumps and a vacuum storage reservoir. The one or more syringe pumps may be replaced by any type of negative positive displacement-type pump such as a piston-in-cylinder, diaphragm pump, bellows, or a non-positive-displacement type device, such as a roots blower, Venturi nozzle with a manually driven air flow (for example though a bulb), turbine, scroll compressor, etc.

Although in the present embodiments, the primary embodiments use a vacuum to transport fluids and to store the manual potential energy used to transport fluid, it should be evident from the disclosure that positive pressure may be used as a means to store energy and transport the fluid from a reverse position. In addition, a positive pressure may be stored and converted by a mechanical pump to negative pressure to transport fluid flow.

Note although the embodiments described in detail show a pump integrated in a portable device, the pump itself may form a separate component that is connected temporarily to the portable assay device in order to store a vacuum or positive pressure and removed. For example, the connection may be made by a self-sealing port as used on volleyballs and footballs. A variety of handheld pumps are commercially available which may be used for this purpose. Preferably where an external pump is used, the storage reservoir includes a pressure relief valve to limit the level of vacuum or overpressure stored in the reservoir.

A generalized embodiment of a diagnostic device 120 is shown in FIG. 1A. The entire system 120 may be embodied in a unitary handheld device with a single housing. Alternatively, as discussed below and above, it may be defined by multiple separate components. In embodiments, a system provides a cartridge receiving support 112 which aligns and positions a cartridge 110 with respect to effectors such as a detector 109 (e.g., a reader) configured to perform an assay, or a fluid displacer 108 which applies a fluid-moving force to fluid in the cartridge 110 (e.g., vacuum or positive pressure) and/or opens and closes vents that control fluid flow. The receiving support 112 may be, or include, a receiving slot for a generally planar cartridge or one with longitudinal edges for engagement therewith. It may include a pin-recess arrangement or any other kind of alignment mechanism. The detector 109 may be a device of any of a variety of types suitable for qualitatively assessing or quantitatively measuring the presence or amount or the functional activity of a target such as cells, reagents, or other analyte of any form. Examples include photodetectors or photomultipliers, chemical sensors, conductivity sensors, etc. The detector 109 may also include a component for changing the environment of the analyte such as a light source for fluorescing analytes or labels, a thermostatically controlled heat source, for incubation or any other type of device to generate a diagnostic result.

The receiving support 112 may be provided with a switch to indicate the presence and proper positioning of the cartridge 110 (i.e., its registration) in the diagnostic device 120. A signal may be applied to the controller 114 to indicate registration of the cartridge 110.

The cartridge may include a microfluidic circuit for storing or receiving an analyte and reagents, probes, labels or other materials required for achieving a desired diagnostic result. Examples go under the common name of a lab on a chip or a microfluidic device. A variety of different types of microfluidic circuit cartridges are described in the patent and non-patent literature. Components of an embodiment, as required for describing examples of interface components such as detector 109 and fluid displacer 108 are described below.

The fluid displacer 108 provides final control, fluid connections, and force for fluid movement within the cartridge 110. In an example embodiment, the fluid displacer connects a vacuum source to a port on the cartridge 110 to transport fluid by suction through the cartridge. In other embodiments, the fluid displacer may also control an air inlet valve to further control the movement of fluid in the cartridge by selectively blocking and permitting vacuum relief upstream of a filled flow channel. A controller 114 may provide control signals to configure the fluid displacer and thereby provide primary control of the flow of fluid in the cartridge. The controller 114, for example, may include a programmable processor. The controller 114 may also provide data acquisition and reduction as well as primary control to/from the detector 109 responsively to commands received through the user interface (UI) 116. A modem and transmitter or transceiver 118 may be provided to, among other things, transmit diagnostic data to a remote location. In embodiments, the modem and transmitter or transceiver 118 is a separate device. In such an arrangement, a single modem and transmitter or transceiver 118 may serve multiple diagnostic devices 120 by allowing them to be connected intermittently to upload stored data (here the controller 114 may include a nonvolatile data store such as a flash drive to store treatment data) which is then communicated to a destination receiver such as a central server. The modem and transmitter or transceiver 118 may be adapted to use the SBD protocol described elsewhere. Data may be stored by the controller 114 in the compact form of FIG. 9 to maximize space or the modem and transmitter or transceiver 118 may include a processor programmed for compressing and encrypting either according to a form such as that in FIG. 9 or some other form.

Storage 106 provides storage of mechanical energy provided by a user through a mechanical actuator 102 and a kinematic mechanism—drive 104—that translates the motion of the actuator to that of an input of the storage 106. In an example, the storage is pressure reservoir (vacuum or positive pressure) and the drive 104 is a positive displacement pump. In other embodiments, the storage 106 is a spring and the fluid displacer includes a pump that is controlled to displace progressively to transport (draw or force) fluid through the cartridge.

A user interface 116 may be provided to receive reduced data from the controller 114 and to receive from a user, and convey to the controller 114, operating commands for the device 120. A modem and transmitter or transceiver may transmit reduced data to remote locations wirelessly, via conductive wires such as wired Ethernet, via satellite, or by any other means or techniques.

Referring now to FIG. 1B, an embodiment of a diagnostic device 120A conforming to the description of diagnostic device 120 in FIG. 1A, has housing elements 128 and 130 which are connected so as to be mutually movable. The relative movement of element 128 with respect to element 130 (illustrated on the right side of the figure) provides a mechanical input that can be translated by a suitable kinematic mechanism to provide the function attributed to mechanical actuator 102 and at least a portion of the drive 104. In an embodiment described below the relative movement of elements 128 and 130 expands a syringe volume to generate a vacuum in a reservoir corresponding to storage 106. The relative movement of the housing elements 128 and 130 can also be used simultaneously to close a switch to generate a signal which begins a diagnostic function in the controller 114 of the diagnostic device 120. For example, the controller 114 may, in response to the switch and an indication that the cartridge 110 is registered, begin a diagnostic operation. The controller 114 may alternatively, in response to the switch and an indication that the cartridge 110 is registered, generate an indication by the user interface 116 that the diagnostic device 120 is ready to perform a diagnostic operation, thereafter providing a virtual control such as a touchscreen button whose activation then initiates the diagnostic function.

FIG. 1C shows an alternative configuration of a diagnostic device 120B in which a pivoting displacement of the elements 132 and 134 supplies a mechanical input. That is, the relative pivoting movement of element 132 with respect to element 134 (illustrated on the right side of the figure) provides a mechanical input that can be translated by a suitable kinematic mechanism to provide the function attributed to mechanical actuator 102 and at least a portion of the drive 104. An example of a suitable kinematic mechanism is described below. In either of the embodiments of FIGS. 1B and 1C, the elements 128 and 130 (or 132 and 134) may serve as housings for components of the diagnostic device 120 and as parts of the mechanical actuator 102. In embodiments, the mechanical actuator 102, drive 104, storage 106 are housed by one element (e.g., 128 or 132) and the user interface 116, modem and transmitter or transceiver 118 are housed by the other. The fluid displacer 108 may be shared between both elements or housed entirely in one as may be the receiving support 112 and cartridge 110. In embodiments, the diagnostic device 120 is provided as a separate system apart from the cartridge 110.

FIGS. 1D and 1E show an example of components that may be used as mechanical actuator 102, drive 104, storage 106, and fluid displacer 108 of FIG. 1A. A cartridge 139 is also shown which corresponds to cartridge 110 of FIG. 1A. A mechanical actuator 150 may be any device for producing a compression and/or expansion of a resilient element 148 illustrated here by a spring, in order to store mechanical energy. A pump, here illustrated by a syringe 146 is progressively displaced by the resilient element 148 generating pressure or a vacuum in cartridge 139 that cause a flow when an inlet (corresponding to vacuum being used to transport fluid) or an outlet (corresponding to positive pressure being used to transport fluid) indicated at 144 is opened by a plug 142. Thus a negative pressure applied by syringe 146 due to the relaxation of the resilient element 148 may draw fluid stored in the cartridge 139 through channels therein when an inlet 144 permits the flow of air into the cartridge 139. A positive pressure may be applied and function to transport fluid similarly. A line may be engaged and disengaged with the cartridge 139 apply the negative or positive pressure thereto.

Figure 2B:
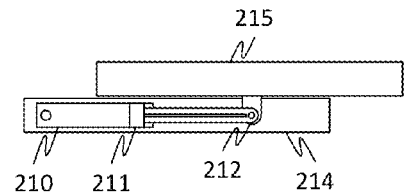

FIGS. 2A and 2B show how a mechanical actuator 102 and drive 104 may work according to the example of FIG. 1B. A housing element 215 is engaged with a sliding element 214, the elements 215 and 214 housing respective components of a diagnostic device 120, for example. Element 215 is attached to an extension 212 that is connected to a piston 211 sliding in a cylinder 210 such that when element 215 is moved as indicated in FIG. 2B, the piston 211 expands the trapped air volume in the cylinder 210. Suitable tubing or direct connections may be provided between the cylinder 210 and a vacuum reservoir to store a vacuum which can then be applied to a microfluidic circuit cartridge such as discussed previously.

Figure 2C:
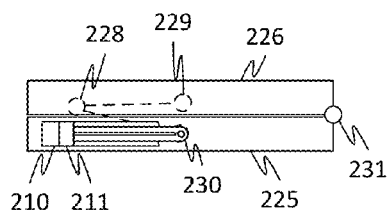
Figure 2D:
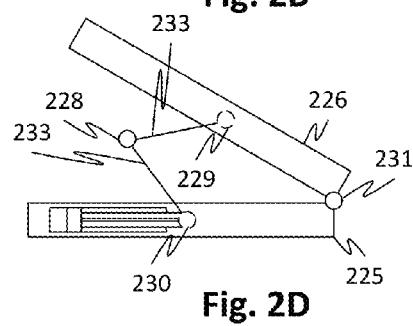
Figure 2E:
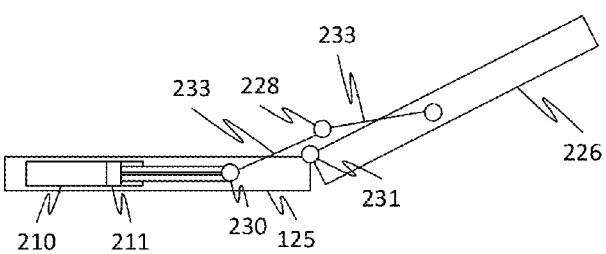

FIGS. 2C, 2D, and 2E show how a mechanical actuator 102 and drive 104 may work according to the example of FIG. 1C. A housing element 226 is engaged with another housing element 225 to pivot on a hinge 231. The elements 226 and 225 may house respective components of a diagnostic device 120, for example. Element 226 is attached at a pivot 229 to a leash having ties 233 interconnected by a hinge 228 such that the leash may pull a piston 211 sliding in a cylinder 210 when element 226 and 225 are mutually hinged open as shown in FIG. 2E. Here again, the piston 211 expands the cylinder 210 trapped air volume. Suitable tubing or direct connections may be provided between the cylinder 210 and a vacuum reservoir to store a vacuum which can then be applied to a microfluidic circuit cartridge such as discussed previously.

Figure 3A:
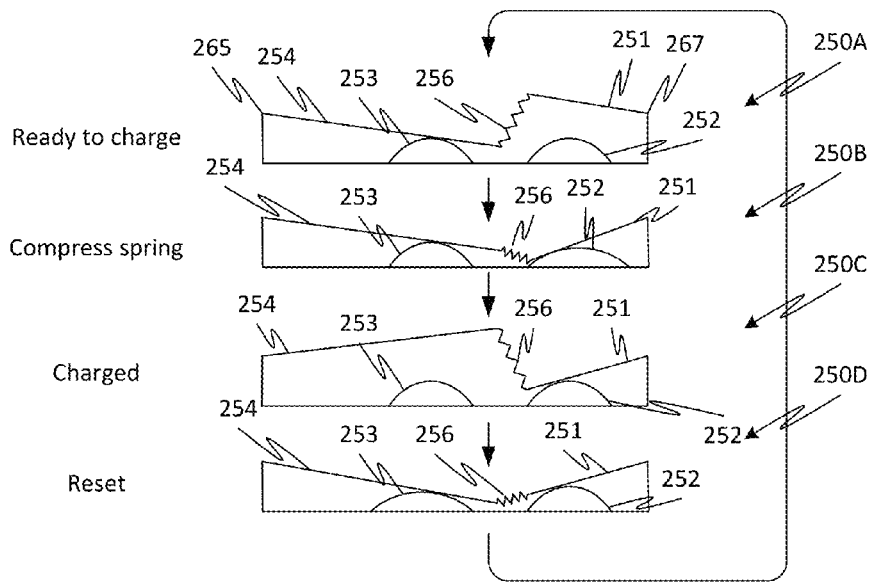
FIG. 3A illustrates a bistable vacuum or pressure generator and storage device that may be used in diagnostic system embodiments of the disclosed subject matter.
Figure 7A:
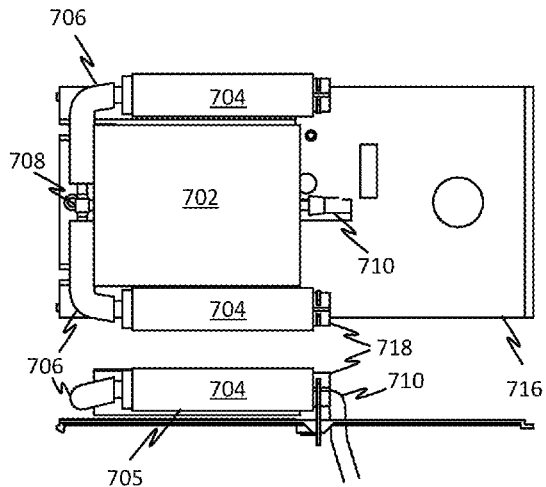
FIGS. 7A through 7D illustrate mechanical vacuum generation features of some embodiments of diagnostic systems elsewhere disclosed herein.

FIG. 3A shows a mechanical bi-stable bellows that encloses a maximum volume in the state indicated at 250C and a minimum volume in the state indicated at 250A. A pair of panels 254 and 251 are interconnected by an expandable portion 256 and pivotable at respective edges thereof 265 and 267, respectively. A pair of leaf springs 253 and 252 allow a selected one of the panels 254 and 252 to be pushed below the level of the opposing one of them such that the expanding portion 256 pushes the opposing one upwardly. At 250A, a minimum volume stable configuration exists. At 250B, the panel 251 is pushed down against the spring 252 so that the edge joining panel 252 to expanding portion 256 is below the edge joining panel 254 and expanding portion 256, thereby allowing the panel 254 to be pushed up. The spring 253 supports the panel 254 so that it is high enough to allow the edge joining panel 252 to expanding portion 256 to be pushed below the edge joining panel 254 and expanding portion 256. The result is the maximum volume stable configuration indicated at 250C. At 250D, the panel 254 is pushed down against the spring 253 so that the edge joining panel 254 to expanding portion 256 is below the edge joining panel 251 and expanding portion 256, thereby allowing the panel 251 to be pushed up. The spring 253 supports the panel 251 so that it is high enough to allow the edge joining panel 254 to expanding portion 256 to be pushed below the edge joining panel 251 and expanding portion 256. The result is the minimum volume stable configuration indicated at 250A. The interior volume of the bistable bellows may create and store a vacuum to be connected by a suitable fluid displacer 108 which may be, for example, configured as the syringe-based design of FIG. 7A. Note that the bi-stable device may be fitted with a check valve, or a user-releasable valve, to equalize it before charging with a positive pressure or vacuum prior to use. For embodiments where a vacuum is used to transport fluid, a check valve that permits air to flow out of the enclosed volume may be used which would equilibrate at the minimum volume configuration. For embodiments where a positive pressure is used to transport fluid, a check valve that permits air to flow into the enclosed volume may be used which would equilibrate at the maximum volume configuration.

Figure 4:
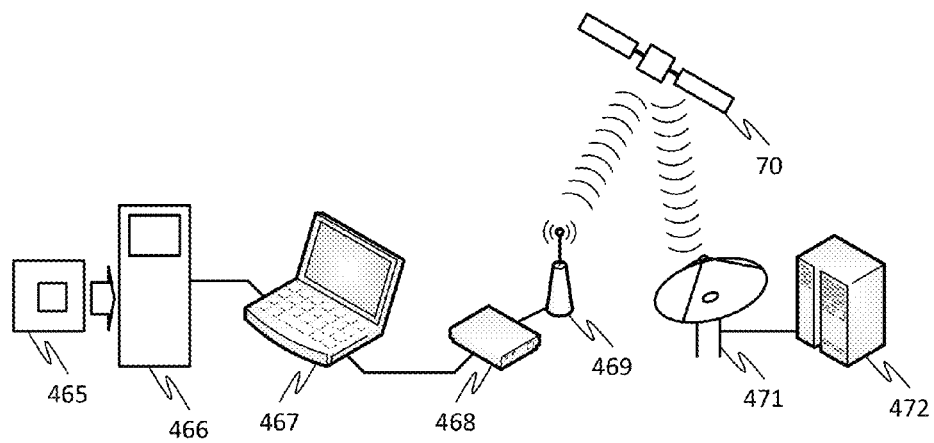
FIG. 4 shows a diagnostic system including data communications components and related systems, according to embodiments of the disclosed subject matter.

FIG. 4 shows an overview of a diagnostic system 466, such as that described above in FIG. 1A and indicated at 120 as well as conforming embodiments described elsewhere in the present specification. A cartridge 465 is engageable with the diagnostic system 466. The features of engagement and operation of the cartridge 465 and the diagnostic system 466 may be as disclosed with regard to any of the embodiments described herein. The diagnostic system 466 is connectable, or incorporates, a processor 467, a modem 468, and an antenna 469 for communication with a satellite 70 which relays diagnostic data to a receiver 471 connected to a data management facility that may use a server 472. Although shown separately, the processor 467, the modem 468, and/or the antenna 469 may be embedded or permanently attached to the diagnostic system 466. Note that in alternative embodiments, communication systems other than satellite based systems may be employed. The satellite system and protocol may be as described below with regard to Short Burst Data (SBD) or equivalent, which is especially advantageous in point of care systems used in rural settings.

Software may be provided on the processor to take in medical data and global positioning system (GPS) data from an embedded or connected GPS system. The software may provide a user interface to accept data from user input. Examples of such data may be found in FIG. 9 and may include data to be combined with the output of the diagnostic system 466.

It will be observed that the diagnostic system 466, and the features described according to embodiments, have particular functions and benefits in the application illustrated in FIG. 4. A small device with low power requirement may be used in a low resource setting, exploiting manual power instead of larger batteries except for short term low power requirements. An external power source may be provided for data communications. In embodiments, the diagnostic device 466 may store diagnostic data in a non-volatile low power data store and be intermittently connected for communication using SBD or some other communication system.

Figure 3B:
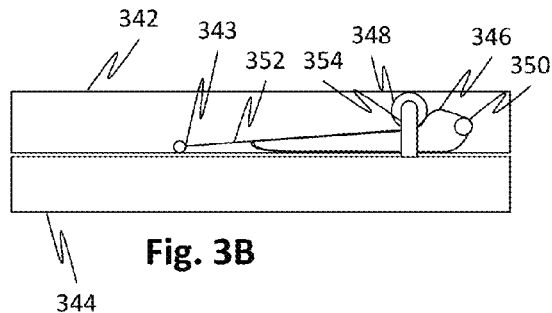
FIGS. 3B-3D shows a further vacuum generator and storage device that may be used in diagnostic system embodiments of the disclosed subject matter.
Figure 3C:
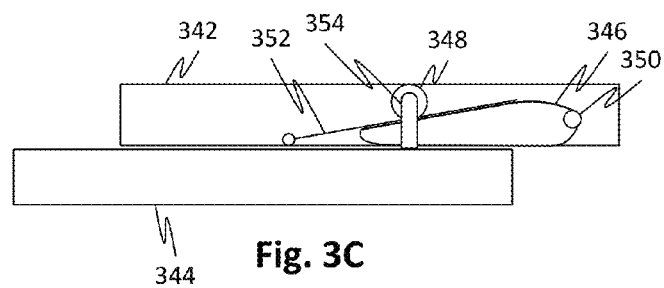
Figure 3D:
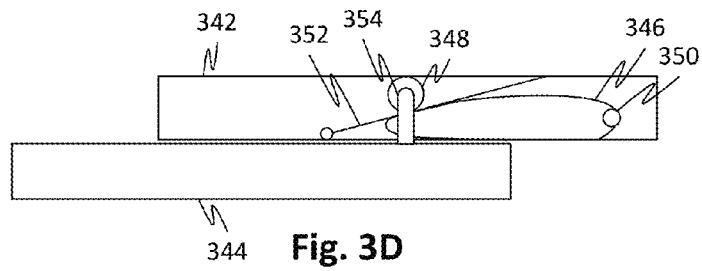

FIGS. 3A, 3B, and 3C show another embodiment of a negative pressure device that may provide the elements of the mechanical actuator 102, the drive 104, and storage 106 of the diagnostic device 120 according to an embodiment. Here mutually displaceable elements 342 and 344 house a bladder 346. A roller 348 rotates on a support 354 attached to element 344 and presses down on a pivoting plate 352 to squeeze the bladder 346 when in the configuration of FIG. 3B. When progressively displaced to relative positions shown in FIGS. 3C and 3D, the plate 352 releases the pressure on the bladder 346 permitting it to expand. The bladder 346 may be enabled to expand passively by including an expanding element within it, such as an-open cell foam, a spring sponge, a mattress spring, or other suitable device, to force it open. For example, the plate 352 may be affixed by adhesive to the bladder 346 and provided with a torsion spring at location indicated by 343 that lifts the plate 352 thereby causing the volume to expand. A port 350 may be connected to a channel to apply a vacuum to a cartridge as discussed with regard to other embodiments herein.

Figure 5:
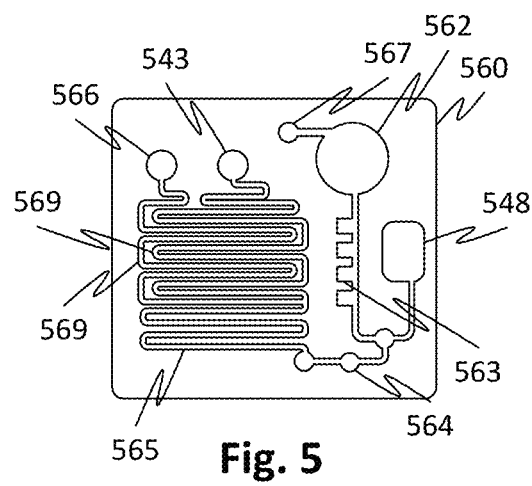
FIG. 5 shows an example of a microfluidic cartridge and some exemplary features to illustrate a way in which a vacuum or pressure source may be used to transport fluid within a microfluidic cartridge, according to embodiments of the disclosed subject matter.

FIG. 5 illustrates an example of a cartridge 560 conforming to the description of the cartridge 110 of FIG. 1A. As mentioned above, diagnostic device 120 of FIG. 1A has multiple embodiments which are described above and below and the cartridge 560 is an example of a cartridge which may interface and/or form part of a diagnostic system as diagnostic device 120 conforming to the description of FIG. 1A and the subtending embodiments or to other embodiments described here or subsystems thereof. This cartridge 560 illustrates possible components and arrangements of a cartridge 110. A suction port 567 has a suction applied to it by a fluid displacer 108. A sump 562 stores waste fluid or overflow. Reaction chambers 563 store reacted species for observation. Chambers 566 and 543 store sample and reagent respectively. Y channel branches 569 feed reagent and sample into a common channel 565, which then flows into the reaction chambers 563 and overflow is captured by the sump 562. To control the flow, an inlet 564 causes air to be drawn by the suction applied at port 567 until the inlet 564 is sealed by a plug, such as a plug 142 described above, or any other kind of sealing device that is controlled by the controller 114 and fluid displacer 108 components. Thus, until the inlet 564 is sealed, the fluids from chambers 566 and 543 are not drawn. In this way, an initial reagent stored in a chamber 548 may be drawn into the reaction chambers 563. Various arrangements of the features and components including various multiples thereof may be provided on a cartridge. For example, multiple closeable inlets such as inlet 564 may be used to control the flow from multiple sources and these may be sequenced as required for the required one or more reactions. The registration of the cartridge with respect to the diagnostic device 120 (and its various embodiments and variants) may provide for the alignment of the control devices and optical interfaces to the cartridge according to any of the embodiments.

Figure 6:
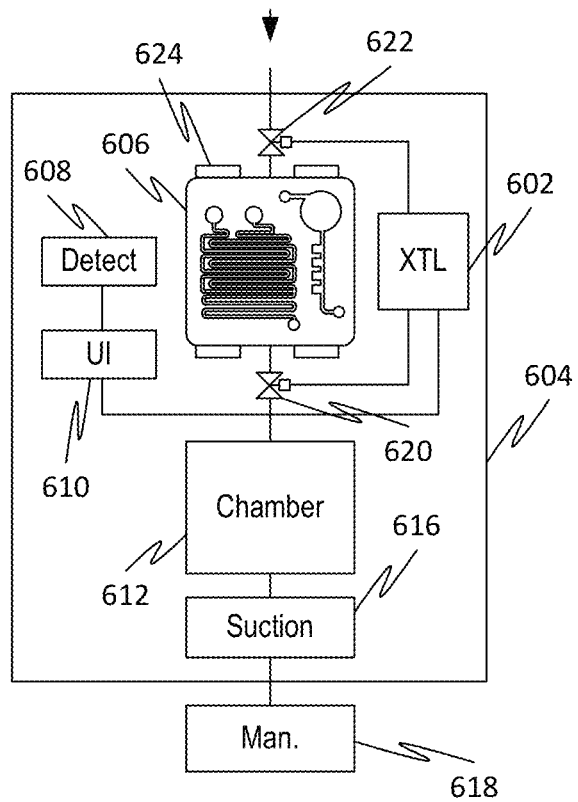
FIG. 6 illustrates features of a diagnostic system relating to detection and control, according to embodiments of the disclosed subject matter.

Referring to FIG. 6, the cartridge 606 is registered in a support 624 and valves 622 and 620 to control inlet and outlet functions are provided according to an embodiment conforming to the diagnostic device 120 of FIG. 1A. A controller 602 controls the valves 622 and 620 of any type which may be a port and plug, an external valve, or any other type to control the flow of air or fluid into or from the cartridge 606. A detector 608 may be provided to detect a feature of the sample in the cartridge. For example, the analyte may be attached to a surface in the cartridge which has been activated with a ligand and caused to fluoresce by a label. In this case the detector may include a light source. A chemiluminescent sample may not require a light source for detection. The presence of analyte or a quantity of analyte may be determined by the detector 608. The controller 602 may perform the flow and detection operations through control of the one or more valves (such as valves 622 and 620) and the detector and may receive signals from the detector 608 which may be reduced and applied to a user interface 610 or stored in a data store for later transmission to a database via a satellite uplink or other means of communication.

Figure 7B:
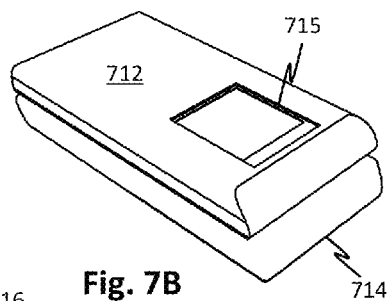
Figure 7C:
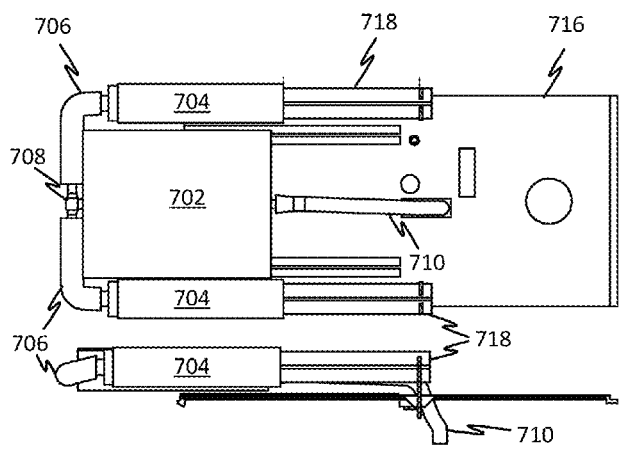
Figure 7D:
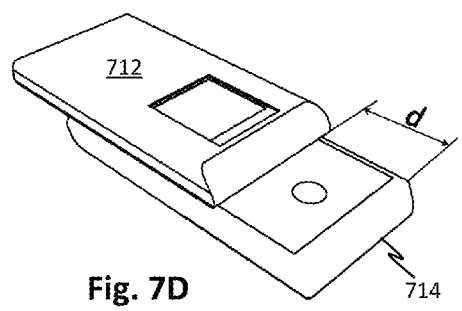

Referring to FIGS. 7A to 7D, an embodiment that provides functionality as described above with regard to FIGS. 1A and 1B is shown in more detail with regard to the mechanical actuator 1012, drive 104, and storage 106 aspects. Also illustrated is an embodiment of a user interface 116. A chamber 702, which may be formed of acrylic or polycarbonate, is connected by tubing 706 and a T-junction 708 to two syringes 704. Each syringe 704 has a cylinder and a piston 718. The medical syringes may be of standard configuration and of, for example, 3 ml nominal capacity. When the device is in a resting position the syringes 704 are at minimum volume positions and their trapped volumes are at equilibrium with the ambient pressure. When a diagnostic assay is run, the housing elements 712 and 714 are moved from the resting position of FIG. 7B to the an activation position indicated in FIG. 7D drawing the syringe pistons to generate a negative pressure in the chamber 702. The negative pressure is applied to a cartridge through a tube 710 attached to the chamber and indicated at 710. The syringes 704 and chamber 702 may be housed in one of the housing elements 712 or 714 and the cartridge supported in the other housing element 714 or 712. The one of the housing elements is affixed to the syringes 704 while the chassis of the other housing element, indicated at 716, is attached to the pistons 718 of the syringes 704. The tube 710 extends to allow the housing elements 712 and 714 to move. A user interface display 715 may be provided in either of the housing elements 712, 714, for example housing element 712 as indicated in FIGS. 7B and 7D. The range of the displacement afforded by the interconnection of the housing elements is indicated as displacement d.

According to Boyle's law: Pressure*Volume=K, where K for a closed system at a stable temperature is a constant. The expanding the volume through the syringes pistons adds to that of the syringes, tubing and chamber, so that the pressure decreases as a consequence of the previous law. Initially the syringe pistons are in the rest position so the total volume is formed mainly by the chamber. The device is activated by sliding one housing element relative to the other housing element. One housing element is connected to syringe pistons and the other to the syringe cylinders and chamber. A supply tube applies the stored vacuum or pressure to a consuming circuit device which may be housed along with control circuits and valving in one of the housing portions. As a result of the sliding displacement of the housing elements the overall system volume is increased (or decreased according to the design) because the syringe pistons get pushed and therefore this extra volume (for example 2.2 ml per syringe) is added to the initial volume of the combined cylinders, tubes, and chamber. In alternative embodiments, the reservoir volume and/or the volume displaced by the syringe may be selected to achieve desired final pressures and capacities.

In an example embodiment, a chamber has a volume of 9.2 $cm^3$ and two syringes with 2.2 ml displacement. By sliding the housing elements, the syringe pistons are displaced to generate and extra volume of 2.2 ml each so that the total volume increases from 18.5 to 22.9 $cm^3$, thereby reducing the pressure from an initial value, for example, of 101 kPa to 82 kPa.

Note that by providing a substantial non-expanding volume portion in the chamber (the actual vacuum-storing reservoir effectively includes the expanded cylinders of the syringes, the tubing, and the chamber), the force required to expand the volumes of the syringes can be selected to be comfortable and easy for a user. This makes it more practical to use in a hand-held device and provide for manual actuation.

An engagement system may be provided, for example in one of the housing elements 712, 714, as described in reference to FIG. 6. The engagement system may connect the cartridge to the fluid transport system for application of a vacuum or positive pressure thereby to move fluid through the cartridge. Further the engagement system may control the timing or sequencing (the order of operations) of connection and the opening and/or closing of ports of the cartridge to permit the flow of fluid therethrough. Note that other devices for controlling the flow of fluid may be used such as described with reference to FIGS. 11A and 11B and many others including control and flow channels separated by a membrane in which the fluid carried by the control channels exerts pressure through the membrane to open and close channels in adjacent flow channels.

FIGS. 7E through 7G show an engagement system 700 embodiment in a first selectable configuration in which a vacuum source is disconnected and a cartridge port is open. FIGS. 7H through 7J show the same engagement system embodiment in a second selectable configuration in which the vacuum source is connected to the cartridge and the cartridge port is still open. FIGS. 7K through 7M show the same engagement system 700 in a third selectable configuration in which the vacuum source is connected to the cartridge and the cartridge port is closed. In the first configuration, a cartridge may be loaded into the associated diagnostic system. In the second configuration, a flow through a first channel arrangement of the cartridge is begun, which is allowed or encouraged by air being permitted to enter the inlet of the cartridge. The third configuration closes the port thereby causing a different pattern of flow in the cartridge. The same embodiment of an engagement system 700 is shown by FIGS. 7E through 7M.

Note that FIGS. 7E, 7H, and 7K are oblique views; FIGS. 7F, 7I, and 7L are plan views, and FIGS. 7G, 7J, and 7M are side elevations.

The engagement system 700 of FIGS. 7E through 7M may be embodied in an electro-mechanical system that can be used to interact with the microfluidic flow system cartridge of any of the embodiments. It may be integrated in one of the housing elements of any of the disclosed diagnostic systems described herein or others. The engagement system embodiment of FIGS. 7E through 7M, is used to connect a vacuum line and to close a valve on a microfluidic cassette, but the general principles and elements may be rearranged, multiplied, and reconfigured to support other types of interactions with a microfluidic cartridge or other device to form other embodiments as will be seen from the description below.

The engagement system 700 employs two levers 750 and 748 that can be pulled down or released using two aluminum moveable sliders 754 and 752 (one for each lever 750 and 748). Each slider 754 and 752 is constrained in position by a bar 738 (which may be made of aluminum, steel, polycarbonate, polyurethane or other suitable material) along which an end of each slider 754, 752 slides. The sliders 752 and 754 threadingly engage with (by means of threaded portions, e.g., nuts 744 affixed thereto), and are driven at their other ends (the ones opposite the ends constrained by the bar 738) by a threaded rod 746 having a drive input end 741 which may be rotated manually or by a motor drive under control of a controller. In an embodiment with a motor, for example, when the motor is activated, the threaded rod 746 rotates and consequently the two sliders 754 and 752 move, pushing down on (or releasing, in the reverse direction) the levers 750 and 748 at particular points along their course of movement. As the sliders 754 and 752 move in a forward direction from a home position shown in FIGS. 7E through 7G to a first position shown in FIGS. 7H through 7J, the first lever 750 is pushed down by the slider 754 forcing a grommet 747 against a vacuum port of a cartridge (the cartridge being as described according to various embodiments elsewhere herein or according to other embodiments known in the art that may be driven by the application of a vacuum). Once this is done, a vacuum may be applied using the mechanical devices described herein. For example, the tube 740 may connect to a vacuum reservoir as described herein which stores a manually-generated vacuum. The force of the grommet pressing against the cartridge seals the tube 740 to the vacuum port of the cartridge. Then when the vacuum is generated, fluid may begin to be transported in the cartridge according to a first flow configuration.

Figures 11A, 11B:
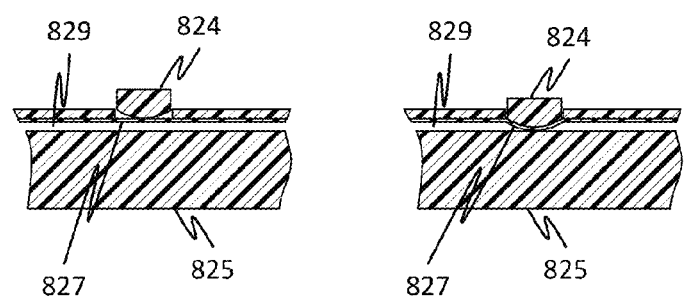
FIGS. 11A and 11B illustrate a flow control device that may be used with the disclosed embodiments.

At a later time, which may be determined by a controller (as in disclosed embodiments) the sliders 754 and 752 are further translated by the threaded rod 746 causing slider 752 to engage and press down lever 748 which pushes against a plug (not shown) which seals a control port of the cartridge. As discussed with reference to embodiments herein the closure of a port of a microfluidic cartridge may reconfigure the flow in the cartridge to cause a second operation of the flow system of the cartridge. In embodiments, instead of sealing a port of the cartridge, a pin may be pushed against a membrane of the cartridge sealing a flow passage therein as illustrated in FIGS. 11A and 11B. A pin 824 may be pushed by a lever as discussed above to press on a membrane 827 thereby sealing a channel 829 formed in a cartridge 825. The channel 829 is shown open in FIG. 11A and closed in FIG. 11B. FIGS. 11A and 11B show a portion of a cartridge 825. Turning the threaded rod 746 in the reverse direction causes the reverse operations to occur ultimately allowing the cartridge to be released. A controller may control the detector to detect properties of materials in the cartridge at a predetermined point after the third configuration is instantiated. This may include an incubation interval. Alternatively, the detection may occur when the configuration returns to the first configuration by the reversal of the threaded rod 746.

Note that other types of actuator mechanisms may be used to produce the actuations described above or others according to different types of cartridges or other microfluidic circuit devices. For example, the sliders may be displaced by rack and pinion mechanism in which the sliders are attached to a rack which is driven manually or by a motor through a pinion engaged therewith.

For example, in an embodiment, a first lever has a PDMS grommet attached on the side that contacts a microfluidic cassette. The grommet may act as housing for a PE tube that is then thereby connected to a vacuum generator system. The second lever has a PDMS cylinder on its bottom side. The PDMS, due to its properties, is able to stick onto the surface (to better adhere and minimize leakage) and at the same time can be easily detached since the retracting force of the steel lever is sufficient to detach it from a plastic medium. The levers may be formed in such a way that they tend to spring upwardly, like leaf springs. Alternatively the sliders may have openings that force the levers up and down depending on the direction of translation.

The first subsystem of the diagnostic device, namely the vacuum system, has beneficial features which include zero power consumption since it is fully mechanical. Also, it does not produce any vibration or noise and is oil free and maintenance free. It is lightweight (in example embodiments, only 46 g), with suitable choice of materials. It can operate in any installed position and can be customized to have the desired pressure and dimensions. It is also low in cost.

The second subsystem of the diagnostic device, namely the engagement system, has beneficial features. For example, it may be embodied as an electro-mechanical module able to contact two different parts at different times or in different sequences. It can be embodied in a low flat configuration with small size such that it can be integrated into a mechanical actuator that can be forced manually to generate a vacuum.

Figures 8, 9:
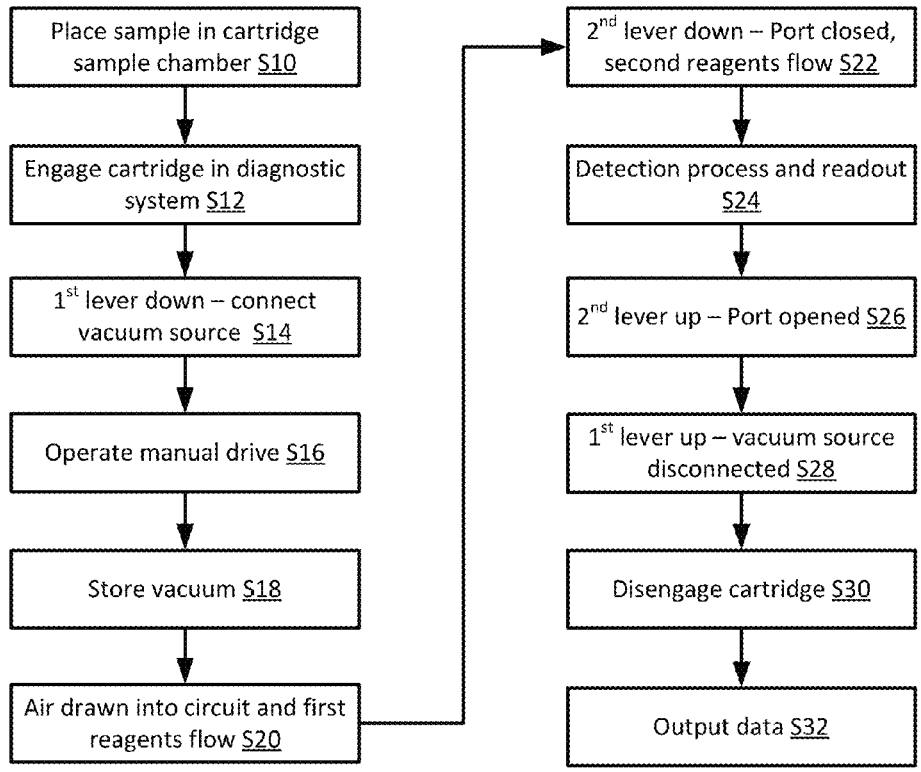
FIG. 8 illustrates a method for using a diagnostic system according to embodiments of the disclosed subject matter.
FIG. 9 shows a communication format for use with embodiments of a diagnostic system described herein and others, according to embodiments of the disclosed subject matter.

FIG. 8 illustrates a method for using a diagnostic system according to embodiments of the disclosed subject matter. The present method is suitable for the embodiment of FIGS. 7A through 7M. At S10, a sample fluid is placed in a receiving part of a cartridge. A variety of devices are known for doing this, for example, a well may be provided or a sample may be injected through a septum into a chamber and directly mixed with a reagent, buffer, or stabilizer. Then the cartridge at S12 is loaded in the diagnostic system and engaged therewith, as discussed elsewhere in the present disclosure. At S14, the vacuum source is connected, for example by pushing down the first lever. Then the vacuum source is operated to store a vacuum in S16 and this may cause an initial fluid flow of fluid in the cartridge S20 as discussed elsewhere herein. At S22 a second phase of operation is initiated by operating a valve or closing a port to cause a second flow of fluid in the cartridge. At S24, a detection process is performed to generate data which may be stored or output immediately (S32). At S26, the engagements steps are performed in reverse to open the valve S26 and disconnect the vacuum source S28 to allow the cartridge to be removed at S30. Data may be output if not already output at S32, for example, by uploading via a satellite link or by transfer to internal or external processor for combination with additional data as described in the present disclosure with regard to the embodiments of the diagnostic system.

One of the challenges in developing a portable nucleic-acid diagnostics device is the need for complex sample preparation. Because DNA and RNA often reside within cells (such as bacteria and human cells) and viral particles, the cells may need to be isolated, lysed, and the nucleic acid contents captured and purified. This sample preparation is often done manually with a centrifuge, making the procedure difficult to implement in a field setting.

An inexpensive, disposable, microfabricated device is disclosed which is used for cell separation and enrichment in milliliter volumes of various sample matrices. Embodiments may be integrated in a cartridge such as cartridge 110 of FIG. 1A and its various embodiments disclosed herein. A method by which the microfabricated device may be employed may include processing a raw sample and subjecting it to nucleic acid amplification and detection. Target-specific isolation may be performed by adding coated magnetic beads to a sample before flowing it through the device. A permanent magnet isolated from the circuit but aligned with a capture chamber immobilizes the beads for detection by a detector (e.g., as described with reference to reader 109 of FIG. 1A). A sample may flow through a vertical chamber for target separation and enrichment and magnetic beads are trapped in the capture chamber, allowing for the rest of sample to pass through an outlet. The design of the vertical chamber allows for a small lateral footprint. Here, the size advantage is obtained by providing a relatively deep chamber rather than the wide shallow design of known systems. The device can process large volumes (~mL) of various sample matrices in minutes, thereby presenting a unique macro-to-micro interface for downstream analytical steps in microfluidic system. It may also enable field processing of small volumes of samples (such as finger-pricked whole blood) diluted in a larger buffer volume containing anticoagulants, magnetic particles, and other useful processing reagents.

Analysis of DNA or RNA sequences can be used in diagnosis of inherited disorders, clinical disease diagnosis (genetic disease, infection, disease staging, drug resistance mutation, and pathogen presence/abundance), and forensic investigations. Nucleic acid testing offers detection that is sensitive (for example, due to amplification) and specific (for example, due to specific base pairing of complementary nucleotides). A microfluidic approach may be employed in which the design and integration of microchips for nucleic acid detection provide the major processing steps of sample preparation, signal amplification, and product detection.

Sample processing, consisting of cell isolation/concentration and lysis followed by nucleic acid extraction and purification, may be performed after biological samples, for example, body fluids, tissues or cells are collected. This step is intrinsically complex. Moreover, contamination, inhibitors for subsequent amplification steps and nucleic acid degradation are also critical and influence diagnostic testing as these factors impede quantitative assessment of the analyte targeted, leading to misinterpretation of results. Traditionally, sample preparation step may be performed off-chip (using laboratory equipment such as centrifuge) while amplification and detection may be accomplished in microfluidic systems. However, microfabrication technology may permit POC tests according to designs that are appropriate for each sample condition and requirement. Integration of sample pre-treatment with analysis leads to improvements in sensitivity (as less of the sample is lost in between steps) and greater convenience.

According to embodiments, the disclosed platform includes a multi-layer microfabricated disposable device, which may be made from inexpensive polymers of various elasticity and an external permanent magnet, or other source of magnetism such as a solenoid, for rapid magnetic bead-bound particle (bacteria, viruses, cells, nucleic acids, antigens, and antibodies) isolation and enrichment of complex sample matrices.

Figure 10A:
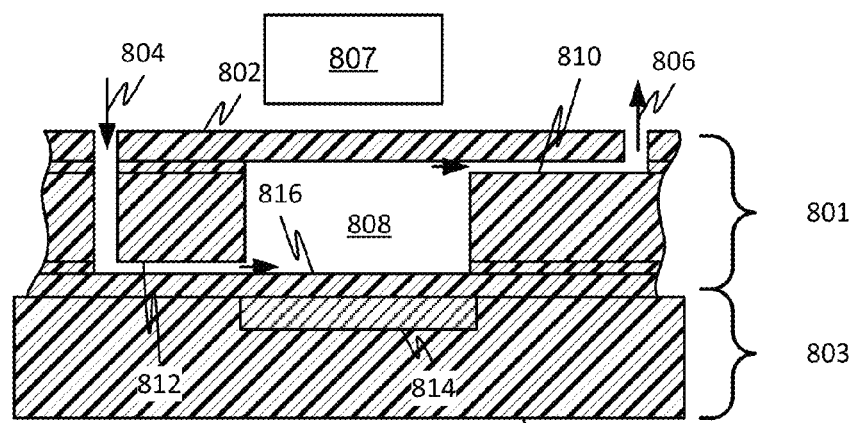
FIGS. 10A and 10B illustrate a flow system for use in microfluidic device that may be used for particle separation and which provides flow-based and magnetic separation features that combine to produce a sampling system, according to embodiments of the disclosed subject matter.
Figure 10B:
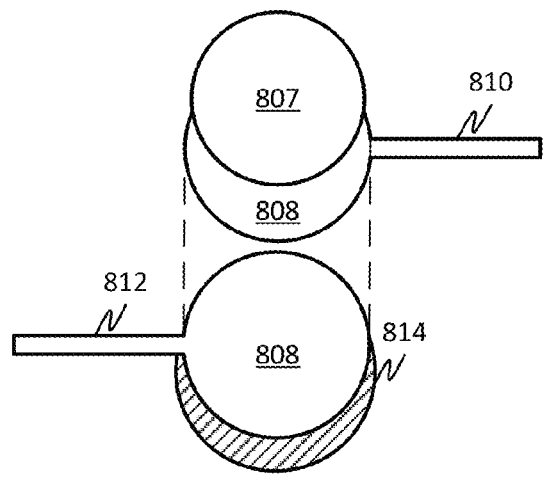

Referring to FIGS. 10A and 10B, a flow system provides rapid target isolation and concentration in a disposable device consisting of two-layer microfabricated device, for example of PDMS. FIG. 10A shows a section and FIG. 10B is a diagonal schematic illustration of the flow path defined. A flow channel with inlet bottom channel 812, chamber 808, and outlet top channel 810 may be fabricated by soft-lithography. Inlet 804 and outlet 806 ports may be provided. A volume, for example having a 10 mm diameter in a layer forms a capture chamber 808. The device may be formed by irreversible bonding of PDMS layers and glass substrate. Plastic tubes may be inserted in or bonded to the inlet 804 and outlet 806. In embodiments, a sample mixed with reagents and microbeads flows through a vertical chamber for target separation and enrichment via the bottom channel 812 to the outlet top channel 810. Larger and heavier particles are trapped in the chamber while the rest of particles, reagents and/or buffer pass through top channel outlet 810. The device can support large volumes of various sample matrices and offers as macro-to-micro interface for microfluidic system.

The flow system can be integrated in a microfluidic cartridge 801 which registers in a diagnostic device 800. In embodiments, a portion of which is indicated at 803 which includes a magnetic source 814 such as a permanent magnet. Target-specific isolation may be performed by adding coated magnetic beads in the sample before flowing it through the device. The magnetic source 814 aligned with the capture chamber traps the magnetic beads. Therefore, non-target substances are not captured and isolated out and flow through the top channel outlet 810. A reader device 807 such as a photodetector or other quantifying or detecting sensing device may be provided that can quantify the analyte concentration for example by detecting light intensity from a suitably labeled analyte. A layer 802 of the microfluidic cartridge 801 may be made transparent to permit a light-detecting reader 807 to capture light from the chamber.

After capture, magnetic beads inside chamber may be washed by flowing wash buffer through while beads are trapped in place with magnetic force and re-suspend in smaller volume and release from chamber for the following step. DNA or RNA extraction can be done with this device by including a heating element at the bottom of chamber for heat lysis. Magnetic beads will also act as heat transfer material to enhance heat exchange.

Experiments have demonstrated that magnetic beads are captured in chamber at 1.0 mL/min flow rate. The configuration of FIGS. 10A and 10B can trap large volume of beads without expanding the footprint, lowering the capture efficiency, clogging flow channel, or shearing targets off from bead surface under high flow rate (mL/min range) when compare to one-layer chamber.

The embodiment of FIGS. 10A and 10B is characterized by a chamber with an inlet channel that is lower than an outlet channel. In embodiments, the chamber is at least 5 times the heights of the inlet or outlet. In embodiments, the inlet and outlet channels have the same height. In embodiments, the inlet and outlet heights are different but each is smaller than a height of the chamber. In embodiments, the chamber is between 5 and 15 mm in diameter. In embodiments, the chamber is cylindrical and in further embodiments, has an aspect ratio (length to diameter) of about unity. In embodiments, the chamber has a non-cylindrical shape but with a height that is at least 5 times greater than the height of the inlet. In embodiments, the inlet is lower than the outlet and there is no vertical span of either that coincides so that the bottom of the outlet is higher than the top of the inlet. In embodiments, the separation between the top of the inlet and the bottom of the outlet is at least twice the height of the chamber. In embodiments, the chamber, the inlet, and the outlet are formed by laminations of materials. In embodiments, a microfluidic cartridge includes a chamber with inlet and outlet channels according to the description of any of the foregoing embodiments in isolation or in any combination. In embodiments, a diagnostic device receives a microfluidic cartridge with a chamber according to the above descriptions and the diagnostic device is configured such that a reader and a magnet are aligned with the chamber when the cartridge is registered therein. The features of these embodiments can be duplicated or varied in cartridges suitably sized and configured.

The foregoing system device can accommodate rapid target-specific sample separation and concentration from large volumes using coated magnetic beads and a vertical chamber capturing technique without a centrifuge which is suited for resource-limited settings. It can also expand to multilayer devices with multiple inlet/outlet for different applications. This platform can also be used for plasma separation from whole blood or liquid-solid extraction from soil for environmental monitoring without centrifugal force.

As described above, a diagnostic device 120 may be provided with a modem and transmitter or transceiver 118 to, among other things, transmit diagnostic data to a remote location. In point-of-care (POC) devices for remote settings, there is a need for communications that can provide digital transport of data, for example by satellite communications.

For example, satellite communications can allow uploading of diagnostic data to a centralized location even from remote locations. Clinical care may be improved with the ability to seamlessly transmit and synchronize the results to the patients' health records (as in tests performed in centralized laboratories). This capability may be valuable for many reasons, for example the reasons may include reduction in human-caused error in data transcription, rapid transmission of results to health experts, improved monitoring of disease outbreaks, and increased effectiveness in allocating medications to different communities. There remains a challenge for POC devices to provide direct digital communication from mobile POC diagnostic devices and to interoperate with patient record databases which are typically located in a central location. Because of prevalent usage (with over 2 billion users) and low cost, cell phones integrated with POC diagnostics are gaining in acceptance. However, current suggested schemes still present challenges including challenges for providing integration, cost, and availability of infrastructure.

In POC diagnostic systems, portable satellite modems may be used to enable global transmission of medical data for mobile health applications. Despite its global coverage, satellite-based data communication (e.g., voice or internet) is generally extremely expensive and not used for routine data transmission. In the present embodiment, a low cost satellite-based data service known as Iridium Short Burst Data (SBD) and a data encoding method are used to enable data transmission for mobile health application at a cost comparable to mobile phone-based SMS. SBD is typically used for maritime vessel tracking or automatic vehicle tracking. It has been virtually unexplored for POC healthcare, but offers potential advantages, for example, high reliability. Satellite phones are the preferred choice for communication in extremely remote areas because they offer universal geographical coverage and do not rely on local infrastructure such as cell-phone towers. Because satellite communication operates independently of the local infrastructure that varies from country to country and over time, it can be rapidly and reliably scaled up to all regions of the world. GPS coordinates may be communicated along with test results to provide information in developing useful statistics. While some portable transceivers are still relatively expensive, difficult to install, and consume large amount of power, transceivers for the Iridium satellite constellation are less expensive, portable, and easy to install and interface. Overall, from anywhere in the world and at low operating cost, this invention enables real-time synchronization of diagnostic data that is encrypted, time-stamped, and geolocation-tagged with an electronic medical record database.

A compact satellite modem (Iridium 9601 SBD Transceiver, 10.6×5.6×1.3 cm) is connected to a POC diagnostic device to communicate diagnostic results directly from a remote setting to a centralized database. The satellite modem operates with a data service called "short burst data" (SBD) provided by the Iridium satellite network. SBD has low operational cost, with minimal latency in data transmission (approximately 5 seconds) and global coverage. The basic architecture of the Iridium system includes the satellite network, the ground network (Earth gateways), and a satellite modem. When a user initiates a data transmission from the field, the modem establishes connection to an overhead satellite, and the encrypted data is relayed among satellites around the globe until it reaches a satellite that is above the appropriate Earth gateway, which downloads the data and sends it as an email to a pre-designated email address via the Internet. An extendable antenna is connected to the POC device to enable RF communication with the satellite.

In order to minimize the size of data to be transmitted (and hence reduce the cost of data transmission), all the data, including date/time of test, patient's information, and test results, are encoded into a 15-byte binary string. As opposed to sending data on a character-by-character basis, a compact messaging format may be used, as shown in FIG. 9, that treats each type of data (e.g., mobile device identifier number, date and time of test, patient identifier number, age, gender, pregnancy status, absorbance values to three decimal places for each of four analysis zones, and error notification) as a numerical value and transmit it as a binary string. This format allows significantly reduced data size and privacy of patient data.

To use the SBD service, a subscription fee of $15 per month and a usage fee of $1.50 per kilobyte (kb) of transmitted data are charged for each registered satellite modem. While transmission of large files is still relatively costly, diagnostic information of each test may be encoded in a tiny 15 bytes binary file (packet) using the messaging protocol of FIG. 9. For 200 POC diagnostics tests a month, the total data transmission cost per test is about 10 cents ($15/200+$1.50/1000*15 bytes=$0.098 per test), comparable to cell-phone based SMS messaging (10-20 cents per message). This also represents a minimal cost compared to approximately $2 of production cost that will be spent per test. Although satellite transceivers tend to be more expensive than cell phones, the cost of satellite transceivers has been decreasing over the years. Today, a satellite transceiver (Iridium SBD 9602) smaller than the size of an iPhone can be purchased commercially for less than $450.

The data transmission system may be adapted to power up by itself to transmit data in one or more 15 byte packets and then to power down until a predefined quantity of data is accumulated in a diagnostic or treatment system. In an advantageous arrangement, a diagnostic system as described with reference to FIG. 1A stores diagnostic data in an on-board nonvolatile data store until a predefined time or event (such as a command to transmit) occurs and then transmits the stored data. The data store may be cleared to make room or maintained as an archive for later use.

The data transmission may be made secure by providing symmetric encryption according the encoding scheme that realizes the compact format. Thus, the encoding can do double duty as a data compression and symmetric key encryption scheme. In embodiments, a 15-byte binary string is generated and transmitted through the satellite network. At the receiving end the string (or strings, if multiple data sets are transmitted at once) are decoded using, for example, a password-protected lookup table. Within the data messages patients may also be identified by compact numerical identifiers according to a secure identification scheme, thereby protecting patient privacy.

In further embodiments, Iridium SBD transceivers are used to transmit data using the Enhanced Mobile Satellite Services (EMSS). EMSS is a Department of Defense (DoD) enhancement to allow commercially available mobile satellite technologies (such as Iridium) to perform data transmission through a DoD dedicated gateway, with features such as end-to-end encryption and protection of sensitive user information.

The messaging scheme of FIG. 9 may be varied for other embodiments and to transport information in addition to or different from that disclosed. Data of types other than assay data from a diagnostic device such as device 120 may be transmitted in other embodiments of a satellite communication system. For example, a device may generate a data signal indicative of:

- a diagnostic indicator of a human from a patient status monitor such as a blood oximeter, electrocardiogram, blood pressure monitor, or any combination of monitors;
- a treatment outcome from a treatment machine that monitors a patient and produces output indicative of the effects of the treatment of a patient, for example ultrafiltrate flow in a renal replacement therapy machine;
- a condition of diagnostic or treatment device indicated by a machine that performs self-monitoring and outputs data that indicates the status of the machine or the existence of a malfunction.

In other types of medical systems as listed above, the communications system described herein may be embedded in a treatment or diagnostic system or provided separately and connected permanently or to uplink periodically to transfer data to a central server.

According to embodiments, the disclosed subject matter may include a point of care medical device. A medical diagnostic or treatment device with at least one sensor is configured to generate digital data responsively to the at least one sensor. The at least one sensor may be adapted to detect and generate a data signal indicative of a result of:

- an assay of a biological substance,
- a diagnostic indicator of a human,
- a treatment outcome, or
- a condition of diagnostic or treatment device.

The device may include a communications component configured to store and compress digital data that may be responsive to the data signal and to wirelessly transmit the digital data. The communications component may be configured to transmit, at transmission times, in packets of less than a kilobyte size. In variations of these embodiments, the communications component may be configured to power down between transmission times. Also, the communications component may operate in conformance with Short-Burst Data (SBD) protocol provided by Iridium satellite communications systems or the Enhanced Mobile Satellite Services (EMSS) protocol used by satellite communications systems or similar communications systems. The packets may include the digital data in encrypted form. The packets may be less than 100 bytes in size and include a patient identifier and diagnostic data.

The foregoing device embodiments may include transmitting the digital data, including directing the digital data for reception by a predefined server for decoding of the digital data. A kit may be formed that may include any of the foregoing devices along with a computer readable medium with instructions encoded thereon for encoding data including a date, a patient identifier, and diagnostic result data pertaining to a patient identified by the patient identifier in a binary encoded compressed and encrypted format. In the kit, the medical diagnostic or treatment device may be configured to perform an assay of a biological substance. Another kit may be include a computer readable medium with instructions encoded thereon for encoding data according to a format as defined in FIG. 9.

In any of the foregoing kit embodiments, the medical diagnostic or treatment device may be configured to perform an assay of a biological substance.

According to embodiments, the disclosed subject matter may include a point of care communications device with a communications device adapted for connection to a diagnostic device and configured for receiving medical diagnostic data generated by the diagnostic device. The data may be responsive to a sensor signal representing a result of an assay of a biological substance. A communications component may be configured to store and compress digital data responsive to the received medical diagnostic data and to wirelessly transmit the digital data. The communications component may be configured to transmit, at transmission times, in packets of less than a kilobyte size in bursts. Each packet can include binary data indicating a patient identifier and the digital data. The communications component may be configured to power down between transmission times. The communications component can operate in conformance with Short-Burst Data (SBD) protocol provided by the Iridium satellite communications systems. The communications component can operate in conformance with Enhanced Mobile Satellite Services (EMSS) protocol used by satellite communications systems. In use, the digital data may be generated for reception by a predefined server for decoding of the digital data.

According to embodiments, another set of embodiment are diagnostic systems for point of care use in remote environments. These include a diagnostic device configured to generate diagnostic data. A controller is programmed to receive diagnostic data from the diagnostic device and to compress and encrypt the data. The controller may be further programmed to receive patient data representing a patient corresponding to the diagnostic data. The controller may be further programmed to compress and encrypt the patient data and the diagnostic data to generate binary data and transmitted using the binary data using Iridium Short Burst Data protocol. The diagnostic device can include a non-volatile data store and may be adapted to store the diagnostic data in the data store. The diagnostic device can include a sensor and an assay platform and may be adapted to perform an assay of a biological substance. The sensor may be arranged to detect a result of an assay. The diagnostic device may be further configured to generate the diagnostic data responsive to a signal from the sensor which may be responsive to the result of the assay.

According to embodiments, the disclosed subject matter also may include a method of providing medical data. The method may include, at a point of care location, operating a portable diagnostic or treatment device to generate diagnostic or treatment data therefrom. The method further may include generating compressed and encrypted data from the diagnostic or treatment data. The method further may include transmitting the compressed and encrypted data by a satellite to a predefine data server. The transmitting may include employing a Short Burst Data transmission protocol. The transmitting may include using a Short Burst Data modem. The method may also include accepting a patient identifier by means of the controller and combining the patient identifier in the diagnostic or treatment data.

According to embodiments, the disclosed subject matter may include a method for performing an assay of a biological substance. The method may include generating vacuum by applying a force to a mechanical actuator and storing a resulting vacuum in a vacuum chamber of a handheld diagnostic device. The force results from manual input to the mechanical actuator without external power input. The method further may include applying vacuum stored in the vacuum chamber to a cartridge may have a microfluidic circuit to transport fluid therein. The applying may include registering the cartridge in the handheld diagnostic device, including aligning a vacuum connector with a port on the cartridge. The method may further include operating a valve of the cartridge using the diagnostic device. The applying may include connecting a channel for fluid communication between the vacuum chamber and the cartridge. The connecting and operating may be performed sequentially by a motor drive with the connecting being performed first. The operating a valve may include sealing an inlet port on the fluid cartridge. The applying a force may include pushing manually on portions of a housing of the diagnostic device. The volume of the vacuum stored in the chamber may be less than 25 cubic cm. The storing may include drawing air from a fixed sized chamber. The method may include using the diagnostic device to operate a valve of the microfluidic cartridge. The applying a force may include translating two elements of a housing of the diagnostic device with respect to each other to drive a positive displacement pump apparatus.

According to embodiments, the disclosed subject matter includes a diagnostic device for performing an assay of a biological substance. The device includes a mechanical actuator and a positive displacement pump mechanically coupled and operating by manual input to the mechanical actuator. A vacuum chamber is connected to the positive displacement pump. The device includes at least one detector and at least one valve actuator. It also includes at least one fluid coupling element open to a vacuum stored in the vacuum chamber or connectable to the vacuum stored in the vacuum chamber. The connector can be, for example, a self-sealing grommet that is pressed against the cartridge to form a sealed channel between the interior fluid circuit of the cartridge and the vacuum chamber. A cartridge support is configured to hold and align a respective portions of a microfluidic cartridge with the at least one detector, the at least one valve actuator, and the at least one fluid coupling element. The detector may be, for example, an optical detector used for an assay. The detector may measure a total amount of light emitted by a part of the cartridge, for example.

The device may include an engagement system that can be configured to connect the at least one fluid coupling element to an inserted cartridge. The engagement system may be configured to sequentially further operate the at least one valve of the cartridge. The engagement system may be powered by a motor. The device may include a controller configured to activate the at least one detector and to control the engagement system. The device may include a housing further include two elements that are movably interconnected, the housing elements enclosing at least respective ones of the positive displacement pump, the vacuum chamber, the at least one, one valve actuator, at least one fluid coupling element, and the cartridge support. The mechanical actuator may be formed in part by the housing elements.

The pump may be configured to generate a vacuum in the vacuum chamber with energy provided by mechanical input to the mechanical actuator, whereby the diagnostic device requires no power source for generating a vacuum. The mechanical actuator may be configured for direct manual operation by manipulating movably interconnected elements of a housing of the diagnostic device.

According to embodiments, the disclosed subject matter includes a pump with a first member attached to a first portion of a positive displacement pump and a second member movably attached to the first member and attached to a second portion of the positive displacement pump. The first and second members may be elongate with their long axes in parallel disposition. the movement of the first and second positive displacement pump portions may be effective to pump a compressible fluid into or from a reservoir when the first and second members are moved relative to each other. One of the first and second members may support a microfluidic circuit connected to the reservoir and a control circuit configured for selectively applying a vacuum or positive pressure to the control circuit which employs power supplied by the vacuum or positive pressure to perform a mechanical function of the microfluidic circuit without the need for power from another source to generate negative or positive pressure. The control circuit may include a mechanism that applies mechanical force to selectively engage and disengage a tube selectively connecting the reservoir to the microfluidic circuit thereby to seal the tube to the microfluidic circuit and a seal to close a vent, the mechanism acting to engage the tube and seal at different times during a single mechanical motion of an actuation member of the control circuit.

According to embodiments, the disclosed subject matter includes a method for removing a first substance from a fluid medium. The method includes suspending magnetic particles coated with an attachment agent to a fluid medium containing the first substance, the attachment agent having a binding affinity for the first substance. The method further includes flowing the fluid medium through a flow channel possessing an external magnetic field sufficient to draw the magnetic particles from the medium leaving a the medium free of the first substance to flow out of the channel. The flow channel may include a chamber with an inlet and an outlet, wherein the inlet may be near a bottom of the chamber and the outlet may be near a top of the chamber and the source of the magnetic field may be proximate the inlet. The external magnetic field may be generated by a permanent magnet. Alternatively, the magnetic field can be generated by a powered solenoid with or without a ferromagnetic core. Other means of creating a magnetic field can also be used. The chamber can have a vertical height at least five times a vertical depth of the inlet or outlet. The method can include providing the flow channel in a microfluidic cartridge, inserting the microfluidic cartridge in a diagnostic device that holds the permanent magnet. The inserting may be effective for aligning the permanent magnet with the chamber. The chamber may be cylindrical with a diameter of no more than 15 mm. The chamber may have a flat surface that lies adjacent the magnet.

According to embodiments of the disclosed subject matter, a diagnostic device has a cartridge support with a magnet. A microfluidic cartridge is engageable with the cartridge support and has a flow circuit therein. The flow circuit includes a chamber. The chamber may have an inlet and an outlet. The chamber may have a flat surface at a first end that lies adjacent the magnet when the cartridge is engaged by the cartridge support. The inlet and outlet may be substantially parallel. The chamber inlet may be adjacent the chamber first end and the chamber outlet may be at an end of the chamber opposite the first end. The chamber may have a height with the chamber inlet and outlet separated across the height. The inlet and outlet may have respective depths and the chamber height may be at least five times a maximum one of the respective depths. The chamber may be cylindrical. The inlet and outlet may be equidistant from an axis of a cylinder defined by the chamber and at opposite sides of the axis. The inlet and outlet may be terminations of respective inlet and outlet channels. The inlet and outlet channels may be parallel. The diameter of the chamber may be no more than 15 mm. The chamber may have an aspect ratio of approximately 1.0. The chamber may have a diameter of 10 mm.

According to embodiments, the disclosed subject matter includes a diagnostic device with a cartridge support that has a magnet. A microfluidic cartridge is engageable with the cartridge support and has a flow circuit therein. The flow circuit has a chamber. The chamber may have an inlet and an outlet that are offset such as to direct incoming fluid in a first direction, then to make a turn in the chamber to flow in a second direction forming a first angle with the first direction. The chamber has a flat surface at a first end that lies adjacent the magnet when the cartridge is engaged by the cartridge support. The inlet is adjacent the first end and the chamber outlet is at an end of the chamber opposite the first end. The microfluidic cartridge may have additional circuit portions and may be generally planar in shape. The second direction can form a second angle with a plane of the microfluidic cartridge. The chamber can have a height with the chamber inlet and outlet separated across the height. The inlet and outlet have respective depths and the chamber height may be at least five times a maximum one of the respective depths. The chamber may be cylindrical. The inlet and outlet may be equidistant from an axis of a cylinder defined by the chamber and at opposite sides of the axis. The inlet and outlet may be terminations of respective inlet and outlet channels. The inlet and outlet channels may be parallel. The diameter of the chamber may be no more than 15 mm. The chamber may have an aspect ratio of approximately 1.0. The chamber may have a diameter of 10 mm. The first angle may be a right angle.

According to embodiments, the disclosed subject matter includes a diagnostic device in which a cartridge support has a magnet. A microfluidic cartridge may be engageable with the cartridge support and has a flow circuit therein. The flow circuit may include a chamber and the chamber may have an inlet and an outlet. The chamber may have a flat surface at a first end that lies adjacent the magnet when the cartridge is engaged by the cartridge support. The chamber inlet may be adjacent the chamber first end, the chamber outlet at an end of the chamber opposite the first end. The chamber having a height, the chamber inlet and outlet may be separated across the height. The inlet and outlet having respective depths, the chamber height may be at least five times a maximum one of the respective depths. The chamber may be cylindrical. The inlet and outlet may be equidistant from an axis of a cylinder defined by the chamber and at opposite sides of the axis. The inlet and outlet may be terminations of respective inlet and outlet channels. The inlet and outlet channels may be parallel. The diameter of the chamber may be no more than 15 mm. The chamber may have an aspect ratio of approximately 1.0. The chamber may have a diameter of 10 mm. The first angle may be a right angle.

It will be appreciated that the modules, processes, systems, and sections described above can be implemented in hardware, hardware programmed by software, software instruction stored on a non-transitory computer readable medium or a combination of the above. For example, a method for assaying cells, communicating diagnostic data, and other features and functions described can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of controllers, communications protocols, and/or computer programming arts.

Moreover, embodiments of the disclosed method, system, and computer program product can be implemented in software executed on a programmed general purpose computer, a special purpose computer, a microprocessor, or the like.

The foregoing descriptions apply, in some cases, to examples generated in a laboratory, but these examples can be extended to production techniques. For example, where quantities and techniques apply to the laboratory examples, they should not be understood as limiting.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, field optimized assay devices, methods, and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicant intends to embrace all such alternatives, modifications, equivalents, and variations that are within the spirit and scope of the present invention.

The invention claimed is:

1. A point of care medical device, comprising:
a medical diagnostic or treatment device with at least one sensor and configured to generate digital data responsively to the at least one sensor;
the at least one sensor being adapted to detect and generate a data signal indicative of: a result of an assay of a biological substance, a diagnostic indicator of a human, a treatment outcome, or a condition of diagnostic or treatment device;
a communications component configured to store and compress digital data that is responsive to the data signal and to wirelessly transmit said digital data; and
the communications component being configured to transmit, at transmission times, in packets of less than a kilobyte size,
wherein the packets include the digital data in encrypted form,
wherein the medical diagnostic or treatment device comprises:
a removable cartridge with on or more microfluidic channels therein;
a pressure generating device constructed to generate a positive or negative pressure;
a storage unit comprising a reservoir that is separate from the pressure generating device and constructed to store the pressure generated by the pressure generating device;
a flow control device including a valve or sealing plug that controls flow through one or more of the microfluidic channels; and
a controller configured to control the flow control device to selectively apply the stored pressure from the storage unit to the one or more microfluidic channels so as to move a reagent and/or the biological substance through the one or more microfluidic channels,
wherein the pressure generating device is constructed to generate the pressure by manual actuation,
the reservoir is constructed to withhold the stored pressure from the cartridge until the flow control device is controlled by the controller to apply the stored pressure to the one or more microfluidic channels,
the one or more microfluidic channels comprise a first inlet for a sample, a second inlet for a reagent, a suction port, and a third inlet,
the third inlet is disposed downstream of the first and second inlets and upstream of the suction port, and
the third inlet allows air to be drawn into the one or more microfluidic channels by a negative pressure applied from the reservoir to the suction port, until the third inlet is sealed by the sealing plug of the flow control device.

2. The device of claim 1, wherein the communications component is configured to power down between transmission times.

3. The device of claim 1, wherein the communications component operates in conformance with Short-Burst Data (SBD) protocol provided by Iridium satellite communications systems.

4. The device of claim 1, wherein the communications component operates in conformance with Enhanced Mobile Satellite Services (EMSS) protocol used by satellite communications systems.

5. The device of claim 1, wherein the packets are less than 100 bytes in size and include a patient identifier and diagnostic data.

6. The device of claim 1, further comprising: a computer readable medium with instructions encoded thereon for encoding data including a date, a patient identifier, and diagnostic result data pertaining to a patient identified by said patient identifier in a binary encoded compressed and encrypted format.

7. The device of claim 6, wherein the medical diagnostic or treatment device is configured to perform an assay of a biological substance.

8. A point of care communications device, comprising:
a diagnostic device comprising:
a cartridge with one or more microfluidic channels therein;
a pressure generating device constructed to generate a positive or negative pressure;
a storage unit comprising a reservoir that is separate from the pressure generating device and is constructed to store the pressure generated by the pressure generating device;
a flow control device including a valve or sealing plug that controls flow through one or more of the microfluidic channels;
a sensor configured to detect a result of an assay of a biological substance and to generate a sensor signal responsively thereto; and
a controller configured to control the flow control device to selectively apply the stored pressure from the storage unit to the one or more microfluidic channels so as to move a reagent and/or the biological substance through the one or more microfluidic channels to perform the assay;
a communication device adapted for connection to the diagnostic device and configured for receiving medical diagnostic data generated by said diagnostic device, the data being responsive to the sensor signal representing the result of the assay of the biological substance;
a communications component configured to store a compress digital data responsive to the received medical diagnostic data and to wirelessly transmit said digital data; and
a power source that provides electrical power to at least one of the controller, the communications device, and the communications component;
the communications component being configured to transmit, at transmission times, in packets of less than a kilobyte size in bursts;
each packet including binary data indicating a patient identifier and said digital data;
the communications component being configured to power down between transmission times, wherein the communications component operates in conformance with at least one of Short-Burst Data (SBD) protocol used by Iridium satellite communications systems and Enhanced Mobile Satellite Services (EMSS) protocol used by satellite communications systems, and the pressure generating device is constructed to generate the pressure by manual actuation without any electrical power from said power source, the reservoir is constructed to withhold the stored pressure from the cartridge until the flow control device is controlled by the controller to apply the stored pressure to the one or more microfluidic channels, the one or more microfluidic channels comprise a first inlet for a sample, a second inlet for a reagent, a suction port, and a third inlet, the third inlet is disposed downstream of the first and second inlets and upstream of the suction port, and the third inlet allows air to be drawn into the one or more microfluid channels by a negative pressure applied from the reservoir to the suction port, until the third inlet is sealed by the sealing plug of the flow control device.

9. A diagnostic system for point of care use in remote environments, comprising:
a diagnostic device configured to generate diagnostic data, the diagnostic device comprising:
  a cartridge with one or more microfluid channels therein, the one or more microfluidic channels including at least a capture chamber, an inlet channel, and or outlet channel, the capture channel being defined by at least a top wall, a bottom wall than the top wall, and the outlet channel being disposed closer to the top wall than the bottom wall;
  a magnetic source disposed closer to the bottom wall than the top wall;
  a pressure generating device constructed to generate a positive or negative pressure;
  a storage unit comprising a reservoir that is separate from the pressure generating device and constructed to store the pressure generated by the pressure generating device; and
  a flow control device including a valve or sealing plug that controls flow through one or more of the microfluidic channels;
a controller configured to control the flow control device to selectively apply the stored pressure from the storage unit to the one or more microfluid channels so as to move fluid through the inlet channel into the capture chamber and out of the capture chamber via the outlet channel such that magnetic beads in the fluid flowing through the capture chamber are retained in the capture chamber,
the controller being programmed to receive diagnostic data from the diagnostic device and to receive patient data representing a patient corresponding to said diagnostic data;
the controller being further programmed to compress and encrypt said patient data and said diagnostic data to generate binary data;
a communication device adapted for transmitting said binary data using Iridium Short Burst Data protocol; and
a power source that provides electrical power to at least one of the communication device and the controller,
wherein the pressure generating device is constructed to generate the pressure by manual actuation without any electrical power from said power source,
the valve of the flow control device controls application of the stored pressure from the reservoir to the cartridge, the one or more microfluidic channels comprise a first inlet for a sample, a second inlet for a reagent, a suction port, and a third inlet, the third inlet is disposed downstream of the first and second inlets and upstream of the suction port, and the third inlet allows air to be drawn into the one or more microfluidic channels by a negative pressure applied from the reservoir to the suction port, until the third inlet is sealed by the sealing plug of the flow control device.

10. The system of claim 9, wherein said diagnostic device includes a non-volatile data store and is adapted to store said diagnostic data therein.

11. The system of claim 9, wherein:
said diagnostic device includes:
  a sensor disposed closer to the top wall than the bottom wall; and
  an assay platform adapted to perform an assay of a biological substance;
said sensor being arranged to detect a result of an assay, and
said diagnostic device is further configured to generate said diagnostic data responsive to a signal from said sensor which is responsive to said result of said assay.

12. A method of providing medical data, comprising:
at a point of care location, operating a portable diagnostic or treatment device to generate diagnostic or treatment data therefrom;
generating compressed and encrypted data from said diagnostic or treatment data;
transmitting said compressed and encrypted data by a satellite to a predefined dataserver,
wherein the operating a portable diagnostic or treatment device comprises:
generating vacuum by applying a force to a mechanical actuator of a pressure generatingdevice of the portable diagnostic or treatment device, the force resulting from manual input to themechanical actuator without external electrical power input;
storing the generated vacuum in a vacuum chamber of the portable diagnostic or treatment device separate from a cartridge having a microfluidic circuit; and
in response to a command from a controller of the portable diagnostic or treatmentdevice, applying the vacuum stored in said vacuum chamber to the cartridge having the microfluidic circuit to transport fluid therein,
wherein the vacuum chamber is separate from the pressure generating device,
wherein the microfluidic circuit comprises one or more microfluidic channels,
the one or more microfluidic channels comprising a first inlet for a sample, a second inlet for a reagent, a suction port, and a third inlet,
the third inlet is disposed downstream of the first and second inlets and upstream of the suction port, and
the third inlet allows air to be drawn into the one or more microfluidic channels by a negative pressure applied from the reservoir to the suction port, until the third inlet is sealed by the sealing plug of the flow control devive.

13. The method of claim 12, wherein said transmitting includes employing a Short Burst Data transmission protocol.

14. The method of claim 12, wherein said transmitting includes using a Short Burst Data modem.

15. The method of claim 12, further comprising accepting a patient identifier, wherein said generating includes combining said patient identifier in said diagnostic or treatment data.

16. The device of claim 1, wherein:
the one or more microfluidic channels includes at least capture chamber, an inlet channel, and an outlet channel;

the capture channel is defined by at least a top wall, a bottom wall, and one or more side walls;

the inlet channel being disposed closer to the bottom wall than the top wall;

the outlet channel being disposed closer to the top wall than the bottom wall;

the medical diagnostic or treatment device further comprising:

a magnetic source disposed closer to the bottom wall than the top wall; and a reader disposed closer to the top wall than the bottom wall; and the controller is configured to control flow from the inlet channel through the capture chamber and out through the outlet channel such that magnetic beads in said flow through the capture chamber are retained in the capture chamber.

17. The medical device of claim 8, wherein:

the one or more microfluidic channels includes at least a capture chamber, an inlet channel, and an outlet channel;

the capture channel is defined by at least a top wall, a bottom wall, and one or more side walls;

the inlet channel being disposed closer to the bottom wall than the top wall;

the outlet channel being disposed closer to the top wall than the bottom wall;

the diagnostic device further comprising:

a magnetic source disposed closer to the bottom wall than the top wall; and a reader disposed closer to the top wall than the bottom wall; and the controller is configured to control flow from the inlet channel through the capture chamber and out through the outlet channel such that magnetic beads in said flow through the capture chamber are retained in the capture chamber.

18. The method of claim 12, wherein the microfluidic circuit includes at least an inlet channel, an outlet channel, and a capture chamber, and the applying vacuum to transport fluid in the microfluidic circuit comprises flowing fluid having magnetic beads therein through the inlet channel into the capture chamber and out of the capture chamber into the outlet channel while applying a magnetic field such that the magnetic beads in the fluid flow are retained in the capture chamber.

19. The device of claim 1, wherein the pressure generating device comprises:

a first member attached to a first portion of a positive displacement pump;

a second member movable attached to the first member and attached to a second portion of the positive displacement pump;

the first and second members being elongate with their long axes in parallel disposition;

the movement of the first and second positive displacement pump portions being effective to pump a compressible fluid into or from the reservoir of the storage unit when the first and second members are moved relative to each other.

\* \* \* \* \*